United States Patent [19]

Minuto

[11] 4,241,084
[45] Dec. 23, 1980

[54] ANTIBACTERIAL AND ANTIFUNGAL COMPOSITIONS

[76] Inventor: Maurice M. Minuto, 15 Hemingway Dr., Dix Hills, N.Y. 11746

[21] Appl. No.: 71,311

[22] Filed: Aug. 30, 1979

Related U.S. Application Data

[63] Continuation-in-part of Ser. No. 39,757, May 17, 1979, abandoned.

[51] Int. Cl.³ .................... A61K 31/18; A61K 31/225
[52] U.S. Cl. ................................. 424/313; 424/321
[58] Field of Search ................................ 424/313, 321

[56] References Cited

U.S. PATENT DOCUMENTS 3,340,148  9/1967  Pugh ...................................... 424/321

OTHER PUBLICATIONS

*Chem. Abstracts* vol. 48, 1954; 139509.
*Chem. Abstracts* vol. 69, 1968; 109830w.

*Primary Examiner*—Frederick E. Waddell
*Attorney, Agent, or Firm*—James W. Badie

[57] ABSTRACT

A novel composition of matter having highly effective antibacterial and antifungal activity as well as other desirable pharmacological properties. The composition is a mixture of a sulfonamide (e.g., toluene sulfonamide), an alkylene glycol in which the alkylene moiety contains 5 to 8 carbon atoms (e.g., hexylene glycol or octylene glycol) and an alkylene glycol ester of an alkylene oxide and a dicarboxylic acid (e.g., propylene oxide ester of sebacic acid).

16 Claims, No Drawings

ANTIBACTERIAL AND ANTIFUNGAL COMPOSITIONS

RELATED APPLICATIONS

This application is a continuation-in-part of application Ser. No. 039,757 filed on May 17, 1979, now abandoned.

FIELD OF INVENTION

This invention relates to a novel composition of matter and is particularly related to a pharmaceutical composition which exhibits remarkable antibacterial and antifungal activity, has anesthetic effects and pronounced vasodilation. More specifically, the present invention is concerned with the treatment of fungus diseases of the skin using these pharmaceutical compositions.

BACKGROUND OF INVENTION

A variety of pharmaceutical compositions or medicaments have heretofore been suggested and used for their antifungal activity in treatment of wounds, skin burns and other fungus diseases of the skin. For example, U.S. Pat. No. 3,340,148 issued to Harry H. Pugh on Sept. 5, 1967 discloses that para-toluenesulfonamide is highly effective for the treatment of fungus diseases of the skin when applied to the affected skin area. According to Pugh, when para-toluenesulfonamide is incorporated in propylene glycol or in formalin to form a solution containing 7 to 10 weight percent (using propylene glycol) or 3 to 7 weight percent (using formalin) of para-toluenesulfonamide, and used as suggested in the aforementioned patent of Pugh, exhibits antifungal or antibacterial activity. However, such low concentrations of para-toluenesulfonamide have limited antibacterial and antifungal activity, and higher concentrations are irritating to the skin and often intolerable. In addition, and so far as it is known, this compound does not have anesthetic effect nor, when administered orally or by injection, show any vasolidation of the cardiovascular system.

It is accordingly an object of this invention to provide a novel pharmaceutical composition and a medicamant which is remarkably effective for treatment of wounds, burns and fungus diseases of the skin by virtue of its unexpectedly high antibacterial and antifungal activity.

It is also an object of this invention to provide such novel compositions which are non-toxic, non-irritating and without adverse effects on the biological system when taken or administered in proper dosage.

It is a further object of this invention to prepare such compositions from readily available ingredients without resorting to cumbersome techniques or specialized equipment.

The foregoing and other objects and properties of the novel compositions of this invention will be described in detail in the ensuing discussion.

SUMMARY OF INVENTION

A novel composition of matter is provided having synergistic antibacterial and antifungal activity which makes it remarkably effective for treatment of skin burns, wounds and fungus diseases of the skin. The composition exhibits other pharmacological activities as well. For example, it is an effective anesthetic and exhibits pronounced tendency to vasolidation of the cardiovascular system.

The improved composition is prepared by blending proper quantities of a sulfonamide represented by the general formula

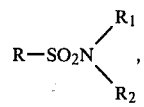

wherein R is an alkyl, aryl, alkaryl or aralkyl radical in which the alkyl moiety contains 1 to 4 carbon atoms, $R_1$ and $R_2$ each is hydrogen or an alkyl radical containing 1 to 8 carbon atoms; alkylene glycol wherein the alkylene radical contains from 5 to 8 carbon atoms, or 2-ethyl 1, 3-hexane diol; and alkylene glycol ester of a dicarboxylic acid in which the alkylene is preferably propylene and the dicarboxylic acid is preferably sebacic acid.

The pharmaceutical composition is prepared by mixing the aforementioned ingredients, in liquid form, until the resulting cloudy or turbid mixture forms a clear solution at which time the preparation is complete.

DETAILED DESCRIPTION OF INVENTION

The pharmaceutical composition of this invention is basically a mixture of the following ingredients:

(1) a sulfonamide, to be hereinafter identified in further detail;

(2) an alkylene glycol in which the alkylene moiety contains 5 to 8 carbon atoms, or a diol to be hereinafter defined, and (3) an alkylene glycol ester of a diacarboxylic acid, e.g., the ester obtained by the reaction of propylene glycol and sebacic acid.

The novel formulation of this invention is prepared by blending the ingredients in a conventional mixer at ambient conditions. The mixture will soon become cloudy or turbid but thereafter forms a clear solution or liquid mixture, at which time blending has been completed.

The order of addition or mixing of the ingredients is not critical to the preparation of the novel compositions. They may be added to the blender in any desired order, or they may all be charged to the blender and mixed together until a clear solution is obtained.

The sulfonamides which are useful in making the pharmaceutical preparations of this invention may be represented by the following general formula:

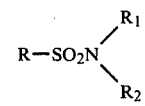

wherein R is an alkyl, aryl, alkaryl or aralkyl group in which the alkyl moiety contains 1 to 4 carbon atoms; $R_1$ is hydrogen or an alkyl group having 1 to 8 carbon atoms, preferably 1 to 3 carbon atoms, or is a cycloalkyl radical, e.g., cyclohexane; $R_2$ is similarly either hydrogen or an alkyl group having 1 to 8 carbon atoms, preferably 1 to 3 carbon atoms, or is a cycloalkyl radical, e.g., cyclohexane, and wherein further $R_1$ and $R_2$ may be the same or different moieties.

Toluene sulfonamide has been found to be particularly desirably and advantageous in preparing the novel pharmaceutical compositions. Other desirable sulfonamides include, but are not limited to, orthotoluene sulfonamide, paratoluene sulfonamide, N-ethyl orthotoluene sulfonamide, N-ethyl paratoluene sulfonamide, N-cyclohexyl paratoluene sulfonamide, or mixtures thereof.

The second ingredient of the novel composition is an alkylene glycol having 5 to 8 carbon atoms, e.g., pentylene glycol, hexylene glycol, heptylene glycol or octylene glycol, or mixtures thereof, with hexylene glycol and octylene glycol consituting the preferred glycols.

Also, and in lieu of the alkylene glycol, or in admixture therewith, 2-ethyl 1,3-hexanediol can be employed efficaciously.

The third ingredient is an ester produced by the reaction of alkylene glycol (e.g., ethylene glycol or propylene glycol) with a dicarboxylic acid (e.g., adipic acid, glutaric acid or sebacic acid). The ester of choice for the preparation of the novel pharmaceutical compositions of this invention is propylene glycol ester or sebacic acid.

The relative amounts of the ingredients will naturally vary somewhat depending upon the particular combination of ingredients used in making the novel preparation. Thus, the sulfonamide component may be used in an amount of from about 50 to 90 weight percent, preferably 60 to 80 weight percent; the amount of the second component may vary from about 1 to about 30 weight percent, preferably from about 5 to about 25 weight percent and the amount of the third component may vary from about 1 to about 10 weight percent, preferably from about 3 to about 8 weight percent.

Typical formulations are as follows:

EXAMPLE I

| 1. | Toluene sulfonamide* | 75% |
|---|---|---|
| 2. | 2-ethyl 1,3-hexanediol | 20% |
| 3. | Propylene glycol ester of dicarboxylic acid** | 5% |

EXAMPLE II

| 1. | Toluene sulfonamide* | 75% |
|---|---|---|
| 2. | Hexylene glycol | 20% |
| 3. | Propylene glycol ester of dicarboxylic acid** | 5% |

EXAMPLE III

| 1. | Toluene sulfonamide* | 75% |
|---|---|---|
| 2. | Octylene glycol | 20% |
| 3. | Propylene glycol ester of dicarboxylic acid* | 5% |

*Sold by the Monsanto Company as Sensitizer 8
**Sold by the Rohm & Haas Company as Paraplex G25

It has been surprisingly found that the novel compositions of this invention exhibit antifungal activity greater than the antifungal activity of the individual components used in preparing these compositions. This difference in activity is believed to be due to the synergistic effect of the combined ingredients as it is evident from the following tests.

In a series of tests, the antibacterial and antifungal activity of the composition of this invention was determined by the so-called method of "Zones of Inhibition" and compared to para-toluenesulfonamide and 2-ethyl 1,3-hexane diol individually. The test procedure generally involves inoculation of agar plates with a live suspension of organisms and placing thereon a sterile disk that was saturated with the test compound. The plates are then incubated and read after a given time interval. The test procedure employed herein may be summarized as follows:

1. 0.05 ml of the test sample was added to a sterile 6 mm disk and allowed to remain in contact therewith for 15 minutes.
2. Trypticase Soy Agar plates were overlayed with 0.02 ml of 1:100 dilution of a 24 hour culture of *E. Coli* N.Y. 1273.
3. Sabouraud dextrose agar plates were overlayed with 0.03 ml of a 1:100 dilution of a 48 hour culture of *C. Albicans* AT 12031.
4. A spore suspension of *T. Mentagrophytes* N.Y. #4 was overlayed on Sabourand dextrose agar plates and another plate was overlayed with the fungi *M. Gypsum* N.Y. #5.
5. The medicated disks were drained and placed on the plates inoculated as in 2-4, supra.
6. The plates inoculated with *E. Coli* was incubated at 35° C. for 24 hours and thereafter left at room temperature for another 48 hours.
7. The plates inoculated with Albicans ATC 10231 were incubated at 35° C. for 48 hours and thereafter left at room temperature for another 48 hours.
8. The plates inoculated with *M. Mentagrophytes* and *M. Gypsum* were incubated at room temperature and read at the end of 7 days.

The above tests were performed using the following test samples:

A. Composition of this invention*
B. para-toluenesulfonamide
C. 2-ethyl 1,3-hexane diol
D. mixture of B and C

*75% para-toluenesulfonamide, 20% 2-ethyl 1,3 hexanediol and 5% propylene glycol ester of dicarboxylic acid All readings were compared to a control disk.

TABLE I

| Test Compound | TSA | BAP |
|---|---|---|
| A | 19, 19, 18, 20, 21, 20 | 20, 20, 21, 20, 20, 20 |
| B | 12, 12, 12, 12, 12, 12 | 14, 14, 14, 12, 12, 12 |
| C | 16, 17, 16, 16, 16, 17 | 16, 15, 17, 16, 15, 16 |
| D | 15, 15, 16, 15, 15, 16 | 14, 14, 14, 12, 12, 12 |
| Control | 0 | 0 |

TABLE II

| Test Compound | C.A. Albicans ATC 10231 | T. Mentagrophytes | M. Gypsum |
|---|---|---|---|
| A | 28,28,25,30,27,30 | 40,40,40,40,40,40 | 48,40,40,34,40,38 |
| B | 12,12,13,12,12,13 | 30,32,30,30,28,30 | 32,33,35,32,31,34 |
| C | 20,19,19,20,19,20 | 35,40,50,50,37,38 | 40,40,40,40,40,40 |
| D | 17,17,16,17,17,16 | 32,32,32,31,34,34 | 30,30,25,27,27,30 |
| Control | 0 | 0 | 0 |

Tables I and II indicate that the compositions of this invention exhibit higher antifungal and antibacterial activity than the individual ingredients used in making these compositions. This increased synergistic activity is evidenced from the consistently higher readings which indicate a higher "kill" rate, and hence, a greater activity.

In other tests, four rats were implanted with five different transplantable tumors and were injected with the compositions of this invention subcutaneously every other day for a total of four injections. The following results were observed:

1. There was no irritation at dose levels of 100 mg/Kg or 400 mg/Kg.
2. At 400 mg/Kg there was marked anesthesia which lasted 4–6 hours.
3. Despite the anesthesia after each injection, there was no cumulative effect and there was good weight gain.
4. There was no outstanding retardation of tumor growth.
5. Over a period of ten days, there were no marked changes in the tests, overies, prostate, uterus or adrenals of the tested rats.
6. There was a pronounced vasolidation of the cardiovascular system.

From the foregoing description and discussion of the various tests, it is evident that the compositions of this invention exhibit remarkable properties which are not exhibited by the individual ingredients used in preparing these compositions.

What is claimed is:

1. A pharmaceutical composition having antibacterial and antifungal activity, which composition consists essentially of:
   (a) from about 50 weight percent to about 90 weight percent of a first ingredient selected from the sulfonamides represented by the general formula

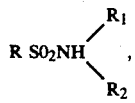

wherein R is an alkyl, aryl, alkaryl or aralkyl radical in which the alkyl moiety contains 1 to 4 carbon atoms; $R_1$ and $R_2$ each is hydrogen or an alkyl radical containing 1 to 8 carbon atoms,
   (b) from about 1 weight percent to about 30 weight percent of a second ingredient selected from the group consisting of alkylene glycol and 2-ethyl 1,3-hexanediol, wherein the alkylene radical contains 5 to 8 carbon atoms, and
   (c) from about 1 weight percent to about 10 weight percent of a third ingredient selected from the group consisting of alkylene glycol ester of a dicarboxylic acid wherein said alkylene radical contains 2 to 4 carbon atoms and said dicarboxylic acid is selected from the group consisting of adipic acid, glutaric acid and sebacic acid.

2. A composition as in claim 1 wherein said R group is toluene and said $R_1$ and $R_2$ are both hydrogen.

3. A composition as in claim 1 wherein said alkylene radical is hexylene or octylene.

4. A composition as in claim 2 wherein said alkylene radical is hexylene or octylene.

5. A composition as in claim 1 wherein said alkylene radical is propylene and said dicarboxylic acid is sebacic acid.

6. A composition as in claim 2 wherein said alkylene radical is propylene and said dicarboxylic acid is sebacic acid.

7. A composition as in claim 3 wherein said alkylene radical is propylene and said dicarboxylic acid is sebacic acid.

8. A composition as in claim 4 wherein said alkylene radical is propylene and said dicarboxylic acid is sebacic acid.

9. A composition as in claim 1 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

10. A composition as in claim 2 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

11. A composition as in claim 3 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

12. A composition as in claim 4 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

13. A composition as in claim 5 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

14. A composition as in claim 6 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

15. A composition as in claim 7 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

16. A composition as in claim 8 wherein the amount of said first ingredient is from about 60 weight percent to about 80 weight percent; the amount of said second ingredient is from about 5 to 25 weight percent and the amount of said third ingredient is from about 3 weight percent to about 8 weight percent.

* * * * *